(12) United States Patent
Ballard et al.

(10) Patent No.: US 7,902,518 B2
(45) Date of Patent: Mar. 8, 2011

(54) NON-INVASIVE BATTERY ANALYSIS VIA MICRO-COMPUTED TOMOGRAPHY

(75) Inventors: Erin L. Ballard, Somerville, MA (US); Craig Buckland, Sandisfield, MA (US); Yang Cao, Farmington, CT (US); Javit A. Drake, Jamaica Plain, MA (US); Thomas Dufresne, Morrow, OH (US); Richard E. Durkot, East Walpole, MA (US); Paul Graham, Taunton, MA (US); Joseph H. Nurre, Cincinnati, OH (US); Philip Trainer, Sandy Hook, CT (US); Darren Trokhan, Hamilton, OH (US); Jonathan Tse, Danbury, CT (US)

(73) Assignee: The Gillette Company, Boston, MA (US)

( * ) Notice: Subject to any disclaimer, the term of this patent is extended or adjusted under 35 U.S.C. 154(b) by 0 days.

(21) Appl. No.: 12/464,483

(22) Filed: May 12, 2009

(65) Prior Publication Data
US 2009/0285358 A1 Nov. 19, 2009

Related U.S. Application Data

(63) Continuation of application No. 12/122,200, filed on May 16, 2008, now Pat. No. 7,550,737.

(51) Int. Cl.
*G01N 23/04* (2006.01)
(52) U.S. Cl. .................. 250/390.06; 250/391

(58) Field of Classification Search ........... 250/391, 250/390.04, 390.01, 390.02, 390.06; 136/290; 378/51, 53, 54, 57, 62, 64, 21, 22, 23, 24, 378/25, 26, 27, 4, 8, 12
See application file for complete search history.

(56) References Cited

U.S. PATENT DOCUMENTS

| 6,904,118 B2 | 6/2005 | Wu et al. | |
|---|---|---|---|
| 7,550,737 B1 * | 6/2009 | Ballard et al. | 250/390.06 |
| 7,662,510 B2 * | 2/2010 | Zhang | 429/164 |
| 2002/0166802 A1 | 11/2002 | Jung | |

FOREIGN PATENT DOCUMENTS

| JP | 6-333605 | 12/1994 |
|---|---|---|
| WO | WO 2005/091225 A1 | 9/2005 |

OTHER PUBLICATIONS

Dr. N. Kardjilov, "n-Tomography", http://www.hmi.de/bereiche/SF/SF3/methods/ntomo/index, Last Revision Aug. 5, 2008.
Manke et al., "In Situ investigation of the discharge of alkaline Znâ€"MnO$_2$ batteries with synchrotron x-ray and neutron tomographies, Applied Physics Letters, vol. 90, May 21, 2007.
Horn et al., "Morphology and Spatial Distribution of ZnO Formed in Discharged Alkaline Zn/MnO$_2$ AA Cells", the Journal of the Electrochemical Society, vol. 150, Issue 5, pp. A652-A658, May 2003.

(Continued)

*Primary Examiner* — David P Porta
*Assistant Examiner* — David S Baker
(74) *Attorney, Agent, or Firm* — Fish & Richardson P.C.

(57) ABSTRACT

A non-invasive multi-step process that includes tomography is applied to determine features of a battery.

8 Claims, 3 Drawing Sheets

OTHER PUBLICATIONS

Cai et al., "In Situ Raman Spectroscopy on an Operating AA Zn-MnO$_2$ Battery Under High Discharge Currents", Electrochemical and Solid State Letters, vol. 3, pp. 319-320, 2000.

Dr. N. Kardjilov, "CONRAD—Lithium Iodide Battery", http://www.hmi.de/bereiche/SF/SF3/materials/complex_engineering_processes/battery/index, Last Revision: Sep. 29, 2006.

"Neutron Imaging, an Essential Tool for the Hydrogen Economy", NIST: Neutron Imaging Facility—Homepage, Dec. 2006.

Ridgway et al., "Water Absorption into Construction Materials: Comparison of Neutron Radiography Data with Network Absorption Models", Transport in Porous Media, vol. 63, pp. 503-525, 2006.

W. Treimer, "Neutron tomography at the HMI, The CONRAD Project", Powerpoint presentation of the Hahn-Meitner-Institut Berlin, Technische Fachhochschule Berlin University of Applied Sciences, Mar. 29, 2004.

Dufresne et al., "Microcomputed Tomography and Its Applications", Encyclopedia of Biomaterials and Biomedical Engineering, Marcel Dekker Inc., 2004.

Mo et al., "In Situ X-Ray Absorption Fine Structure Studies of a Manganese Dioxide Electrode in a Rechargeable MnO$_2$/Zn Alkaline Battery Environment", Journal of the Electrochemical Society, vol. 144, Issue 5, pp. 1598-1603, May 1997.

Ulrich et al., "The quality of trabecular bone evaluated with microcomputed tomography, FEA and mechanical testing", Bone Research in Biomechanics, pp. 97-112, 1997.

Thurston et al., "Synchrotron x-ray diffraction studies of the structural properties of electrode materials in operating battery cells", Appl. Phys. Lett., vol. 69, No. 2, pp. 194-196, Jul. 8, 1996.

Ruegsegger et al., "A Microtomographic System for the Nondestructive Evaluation of Bone Architecture", Calcif Tissue Int., vol. 58, pp. 24-29, 1996.

Dr. I. Manke, "Alkaline Batteries—BAMline", http://www.hmi.de/bereiche/SF/SF3/materials/complex_engineering_processes/A1_battery, Undated.

Kardjilov et al., "Industrial applications at the new cold neutron radiography and tomography facilty of the HMI", Nuclear Instruments and Methods in Physics Research, A 542, pp. 16-21, 2005.

* cited by examiner

NON-INVASIVE BATTERY ANALYSIS VIA MICRO-COMPUTED TOMOGRAPHY

CROSS REFERENCE TO RELATED APPLICATIONS

This application is a continuation of and claims the benefit of priority under 35 U.S.C. §120 to U.S. application Ser. No. 12/122,200, filed on May 16, 2008, now U.S. Pat. No. 7,550,737, issued on Jun. 23, 2009. The contents of the parent application is hereby incorporated by reference in its entirety.

TECHNICAL FIELD

This invention relates to batteries.

BACKGROUND

Batteries are commonly used as electrical energy sources. A battery contains a negative electrode, typically called the anode, and a positive electrode, typically called the cathode. The anode contains an active material that can be oxidized. The cathode contains or consumes an active material that can be reduced. The anode active material is capable of reducing the cathode active material.

When a battery is used as an electrical energy source in a device, electrical contact is made to the anode and the cathode, allowing electrons to flow through the device and permitting the respective oxidation and reduction reactions to occur to provide electrical power. An electrolyte in contact with the anode and the cathode contains ions that flow through the separator between the electrodes to maintain charge balance throughout the battery during discharge.

SUMMARY

Generally, the invention relates to performing tomography on a battery. Tomography is imaging by sections or sectioning. Examples of tomography include computed tomography (or X-ray tomography), neutron tomography, and cryo-electron tomography. Tomography provides a non-invasive and non-destructive technique for acquiring information concerning the battery.

In one aspect, the invention provides a method of determining a feature of a battery that has an interior. The method includes using tomography to acquire data non-invasively for the interior of the battery and determining a feature from the data.

In another aspect, the invention provides a method of acquiring data concerning the interior of a battery. The method includes isolating a component and/or an area in the interior of the battery and using tomography to acquire data non-invasively for the interior of the battery.

In another aspect, the invention provides a method of determining a feature of a battery that has an interior. The method includes using tomography to acquire data non-invasively for the interior of the battery when the battery is un-discharged, for example, a first volume within the battery can be obtained, discharging the battery, and using tomography to acquire data non-invasively for the interior of the discharged battery, for example, a second volume within the discharged battery can be obtained. A discharge behavior of the battery can be determined from the first and second volumes.

Embodiments may include one or more of the following features. The feature can be determined by generating a three-dimensional representation of the interior from the data. The feature can be occupied space, un-occupied space, volume of the unoccupied space, density, for example, of a component of the battery, such as the cathode, hydrogen gas, hydrogen-containing molecules in the battery and/or water in the battery. The feature can concern a component or portion of the battery or the entire battery. The feature can be determined at multiple positions in the interior of the battery. For example, the battery can include a cathode and the feature can include cathode density measured at multiple positions in the interior of the battery. A variation of the feature at the multiple positions in the interior of the battery can be determined. The battery can include a component and the feature can be a distribution of the component in the interior of the battery. The density at multiple positions can include stack edge artifacts, which can be mitigated by combining multiple scans of the battery with staggered starting positions. For example, to mitigate the artifacts, a two pass scanning approach that includes a first scan and a second scan can be employed. The starting position of the battery in the second scan can be offset by half of the height of a stack. Each scan can produce central stack data. The splicing of the central stack data associated with the two scans can eliminate the stack edge artifacts.

Embodiments may also include one or more of the following features. A component and/or an area in the interior of the battery can be isolated or stratified prior to using tomography to acquire data non-invasively for the interior of the battery. The component and/or the area of the battery can be isolated by applying a force to the intact battery. The component and/or the area of the battery can be isolated using, for example, gravity, concentric force, temperature, or magnetism. A void can be isolated at an end of the battery.

Embodiments may also include one or more of the following features. After determining the internal features, the interior of the battery can be physically accessed and an analysis can be conducted. The analysis can be a chemical analysis. Tomography can be used before, during, and/or after the battery is discharged. The battery can be discharged repeatedly and tomography can be used repeatedly to acquire data non-invasively for the interior of the discharging battery. The component and/or the area of the battery can be isolated by applying a force, for example, gravity or concentric force, to the battery before, during, and/or after the battery is discharged and before tomography is used.

Embodiments may also include one or more of the following features. The tomography can be micro-computed tomography. The battery can rotate within a micro-computed tomography instrument with respect to an axis of symmetry (e.g. the longitudinal axis) of the battery. Using micro-tomography can include applying X-ray beams from an X-ray source on the battery. The X-ray beam can be filtered using a filter. The filter can include a metallic material. The metallic material can be selected from the group consisting of aluminum, zinc, iron, copper, brass, bronze, nickel, titanium, and combinations thereof. The filter can have a thickness, for example, of about 0.01 mm, 0.02 mm, and/or up to, for example, about 1.00 mm. The energy profile of the X-ray beams can be adjusted before applying the X-ray beams on the battery, for example, by adjusting a thickness of the filter, component of the filter, the voltage and/or the current of the instrument. An X-ray spectrometer can be coupled to the X-ray source. The tomography can also be neutron tomography. The tomography can be conducted at room temperature.

The methods can be used on primary or secondary batteries. Primary electrochemical cells are meant to be discharged, e.g., to exhaustion, only once, and then discarded. Primary cells are not intended to be recharged. Primary cells are described, for example, in David Linden, Handbook of Batteries (McGraw-Hill, 2d ed. 1995). Secondary electrochemical cells can be recharged for many times, e.g., more than fifty times, more than a hundred times, or more. Secondary cells are described, e.g., in Falk & Salkind, "Alkaline Storage Batteries", John Wiley & Sons, Inc. 1969; U.S. Pat. No. 345,124; and French Patent No. 164,681.

The methods can be used on any type of batteries, such as alkaline batteries, lithium-ion disulfide batteries, lithium-phosphate batteries, lithium-manganese dioxide batteries, zinc air batteries, zinc-carbon batteries, nickel-metal hydride batteries, lithium ion batteries, plumbum acid batteries, and silver zinc batteries.

The methods can be used on batteries of any shape, such as cylindrical batteries (e.g., AA, AAA, AAAA, C, and D batteries), prismatic batteries (e.g., PP3 battery), and button batteries (e.g., watch batteries).

The methods can be used in battery design and modeling.

All publications, patent applications, patents, and other references mentioned herein are incorporated by reference herein in their entirety.

Other features and advantages of the invention will be apparent from the following detailed description, and from the claims.

DESCRIPTION OF DRAWINGS

Like reference symbols in the various drawings indicate like elements.

DETAILED DESCRIPTION

Figure 1:
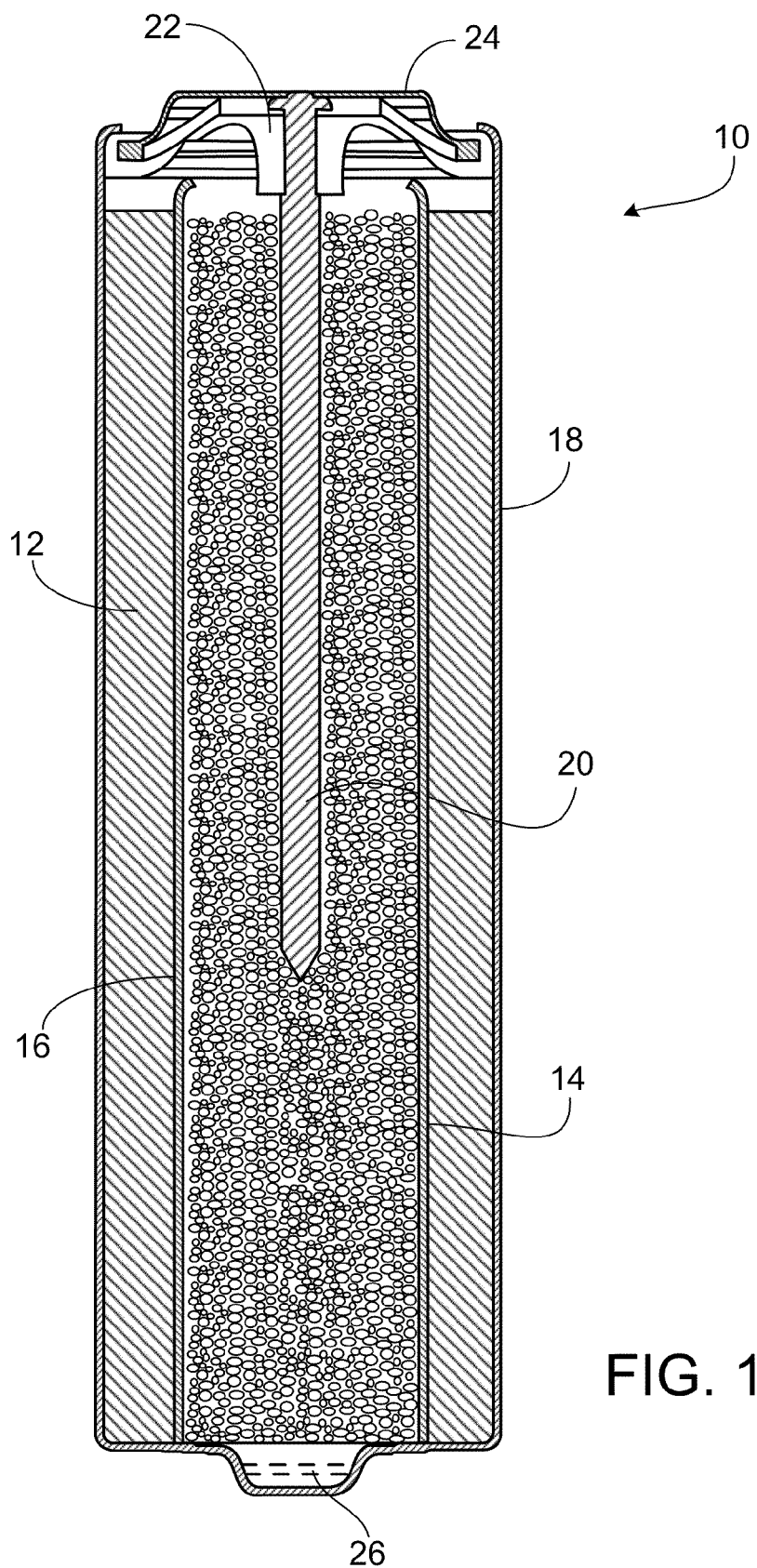
FIG. 1 is a schematic diagram of a battery.

Referring to FIG. 1, battery 10 includes a cathode 12, an anode 14, a separator 16 and a cylindrical housing 18. Battery 10 also includes current collector 20, seal 22, and a negative metal end cap 24, which serves as the negative terminal for the battery. A positive pip 26, which serves the positive terminal of the battery, is at the opposite end of the battery from the negative terminal. An electrolytic solution is dispersed throughout battery 10. Battery 10 can be an alkaline battery, for example, a AA, AAA, AAAA, C, or D battery.

Cathode 12 includes one or more cathode active materials. It may also include carbon particles, a binder, and other additives. Examples of cathode active material include manganese dioxide, and nickel oxyhydroxide. The carbon particles may be graphite particles. Examples of binders include polyethylene, polyacrylic acid, or a fluorocarbon resin. An electrolyte solution can be dispersed through cathode 12. The electrolyte can be an aqueous solution of alkali hydroxide, such as potassium hydroxide or sodium hydroxide.

Anode 14 can be formed of an anode active material, a gelling agent, and minor amounts of additives, such as gassing inhibitor. In addition, a portion of the electrolyte solution discussed above is dispersed throughout the anode. Examples of the anode active material include zinc. Examples of a gelling agent can include a polyacrylic acid, a grafted starch material, a salt of a polyacrylic acid, a carboxymethylcellulose, a salt of a carboxymethylcellulose (e.g., sodium carboxymethylcellulose) or combinations thereof. A gassing inhibitor can include an inorganic material, such as bismuth, tin, or indium. Alternatively, a gassing inhibitor can include an organic compound, such as a phosphate ester, an ionic surfactant or a nonionic surfactant.

Separator 16 can be a conventional alkaline battery separator. In other embodiments, separator 16 can include a layer of cellophane combined with a layer of non-woven material. The separator also can include an additional layer of non-woven material. Housing 18 can be a conventional housing commonly used in primary alkaline batteries, for example, nickel plated cold-rolled steel. Current collector 20 can be made from a suitable metal, such as brass. Seal 22 can be made, for example, of a nylon.

Battery 10 includes un-occupied space, i.e., space that is occupied by gas or liquid but not occupied by solid components of the battery. For example, components of battery 10, such as cathode 12 and anode 14 include pores or voids as un-occupied space. Thus, the components in battery 10 occupy less space than the total volume within housing 18. The un-occupied space provides a reservoir for generated gas, e.g., hydrogen, and room for the expansion of the anode and cathode materials during the use of the battery. The un-occupied space can effectively provide a buffer in battery 10 to adjust the internal pressure. The control of the volume of the un-occupied space can help control gas generation and battery performance.

Figure 2:
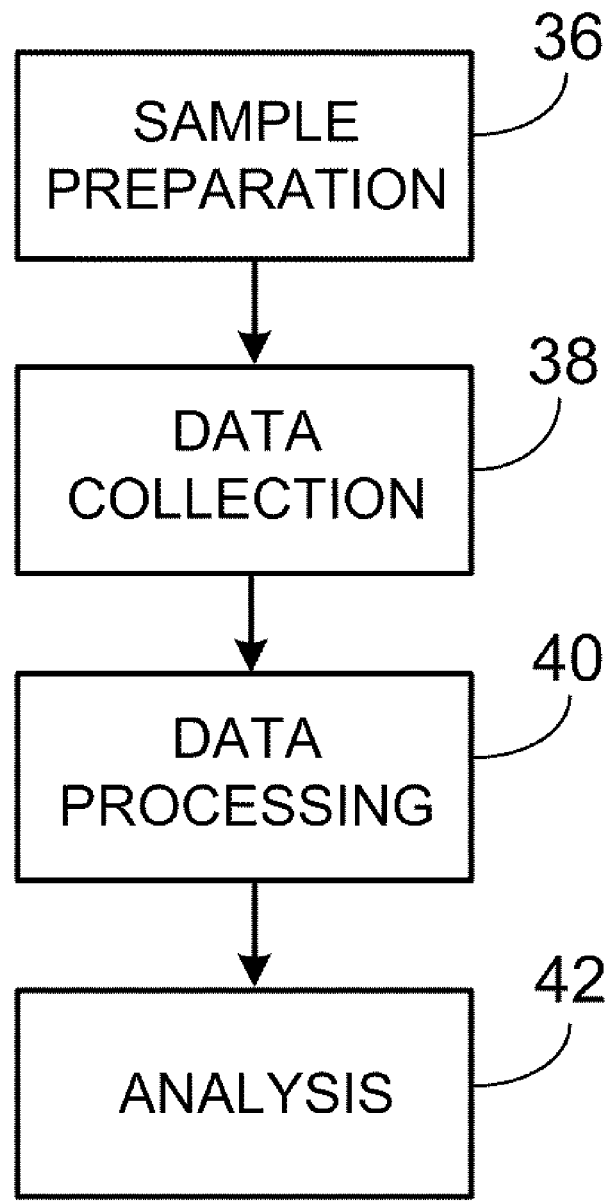
FIG. 2 is a flow chart exemplifying a method of determining an internal feature of a battery.

A non-invasive multi-step process can be used to determine an internal feature of battery 10, such as un-occupied space. Referring to FIG. 2, the process includes a sample preparation step 36, data collection step 38, data processing step 40, and analysis step 42. As used herein, non-invasive means without physically opening the battery.

In addition to occupied space, the internal feature can be, for example, the volume, density, porosity, and distribution of the various components, such as cathode 12 or anode 14, in battery 10. In some embodiments, the internal feature is related to the entire battery 10. In some embodiments, the internal feature is related to a portion of battery 10, e.g., a specific location or area. The internal feature can be evaluated before, during, and/or after the discharge process. Measurement and determination of the internal feature can facilitate better design of batteries and enhance battery performance.

In some embodiments, sample preparation step 36 includes non-invasively stratifying or isolating components or areas of battery 10 using gravity or centrifugal forces. For example, the un-occupied space can be isolated to an end, e.g., the positive end, of battery 10 by shaking or spinning.

During the data collection step 38, data or images of battery 10 are collected using micro-computed tomography (mCT). mCT employs tomography where digital geometry processing is used to generate a three-dimensional image of the internals of an object from a large series of two-dimensional X-ray images taken around a single axis of rotation. Detailed information about mCT is also provided in Dufresne et al., "*Microcomputed Tomography and Its Applications*" in *Encyclopedia of Biomaterials and Biomedical Engineering, Marcel Dekker Inc.*, 2004; Ruegsegger et al., *A microtomographic system for the non-destructive evaluation of bone architecture, Calcif. Tiss. Int.* 58, 24-29 (1996); and Ulrich et al., "*The quality of trabecular bone evaluated with micro-computed tomography, FEA and mechanical testing*" in *Bone Research in Biomechanics, IOS Press Amsterdam*, 97-112, 1997.

In some embodiments, the X-ray from the X-ray source is filtered before applied on battery 10. For example, a filter made, for example, of Al or Zn is applied between the X-ray source and battery 10. The filter can have a thickness of about 0.01 mm to about 1 mm. In some embodiments, more than one filter is used.

In some embodiments, an X-ray spectrometer is coupled to the filtered X-ray source and used in conjunction with the mCT instrument. The spectrometer can measure the properties, such as energy profile, of the filtered X-ray source and facilitate optimizing and controlling the filtering of the X-ray source.

Battery 10 is placed within a radiation tube of an mCT instrument, e.g., SkyScan 1172, with the longitudinal axis of battery 10 aligned with the axis of rotation. The area of interest within battery 10 may be, for example, a section of the anode 14. In some embodiments, before placing the battery in the radiation tube to conduct the micro-computed tomography on the battery, the radiation tube is warmed up, for example, for at least 8 minutes or at least 30 minutes.

The X-ray images from different angular views represent two-dimensional cross-sectional images of battery 10. These images can be processed in the data processing step 40 and reconstructed to form a three-dimensional microstructure image based on the contrast in X-ray absorption of the components of battery 10 using software products, such as MatLab and Amira, as well as user defined coding. Other image process and/or analysis platforms can also be used. Examples of such platforms include Analyze® (AnalyzeDirect, Overland Park, Kans.), TVK® (Kitware, Clifton Park, YN), ImagePro Plus® (MedicalCybernetics, Bethesda, Md.), and ImageJ® (Open Source, NIH).

Finally, the reconstructed three-dimensional microstructure image is analyzed in the analysis step 42 to quantify internal features of battery 10.

The non-invasive multi-step process using micro-computed tomography can characterize the features of the various components of battery 10 with high precision, for example, to a micro scale. Due to the non-invasive characteristics of the processes, the information obtained for the interior of a sealed battery is valuable in designing, manufacturing, and quality assurance of batteries.

In some embodiments, neutron tomography can be used for data collection. Neutrons are effective in probing elements such as hydrogen, lithium$_6$, boron$_{10}$, calcium, and gadolinium, even when these elements are encased in metal housings. Hence, substances with dense concentrations of these elements (e.g., liquids or solids containing these elements) are amenable to neutron tomography. For example, substances that contain the hydrogen element include water, hydrogen peroxide, and organic hydrogen-containing compounds and mixtures. Therefore, neutron tomography enables the imaging of the distribution of electrolyte and the electrode (when the electrode is made of lithium) within battery 10, both spatially and dynamically. Similar to micro-computed tomography discussed previously, two dimensional images of battery 10 can be generated and processed to reconstruct a three-dimensional representation of the interior of battery 10. Discussion of neutron tomography is also provided in Ridgway et al, *Trans. in Porous Media* 63, 503-525 (2006).

In some embodiments, the multi-step process described above can be used to understand the dynamic evolution, for example, discharge behavior of one or more components of battery 10. In such embodiments, a number of three-dimensional images are generated before, during, and after the discharge of battery 10. For example, after sample preparation, micro-computed tomography is applied on un-discharged battery 10 and through analysis a first three-dimensional image of the battery is generated. Battery 10 is then discharged and micro-tomography is applied again to generate a second three-dimensional microstructure image of battery 10. The discharge process and the data collection and process steps can be applied repeatedly to produce more three-dimensional images of the discharging battery 10.

The three-dimensional images are analyzed in a time sequence to depict the dynamic evolution, for example, expansion of the cathode or anode active materials, the distribution and density changes of different components, and distortion of the battery during the discharge process. In some embodiments, components or areas of interest are examined with focus so that the dynamics of the specific components or areas can be tracked. Desired information can be obtained by controlling, for example, the duration and times of the discharge process.

In some embodiments, after obtaining the three-dimensional image of battery 10, an invasive chemical analysis is conducted on battery 10. In such embodiments, battery 10 is opened and the occupied space, for example, the distribution of active materials is analyzed. The application of the combined non-invasive multi-step process and invasive chemical analysis on the same battery allows connection of the physical properties, for example, from the three-dimensional images of a battery, to the chemical properties of the same battery.

Although the non-invasive process and related analysis described above are applied on alkaline battery 10, they can be used on other batteries, for example, lithium-iron disulfide, lithium-phosphate, lithium-manganese dioxide, zinc air, zinc-carbon, nickel-metal hydride, and lithium ion batteries. The non-invasive process and related analysis described above can be used in battery design and modeling.

EXAMPLES

Example 1

In this illustrate example, the cathode volume of a AA battery is non-invasively measured and calculated.

A commercial AA battery is provided and placed in a mCT system for scanning. The battery is rotated at a step size of about 0.9 degree/180 degrees. Each step generates one X-ray projection data file. 1800 projections are taken and the corresponding 1800 data files are processed and reconstructed using a standard cone beam algorithm to produce a stack of image slices, which construct the three-dimensional AA battery under study. Using thresholding and connected components labeling, the region of the cathode is identified in each slice. The area of the cathode region in each slice is calculated and the cathode volume is the sum of the cathode area from all slices.

Example 2

In this illustrative example, using mCT, the void volume of a AA battery is non-invasively measured and calculated.

Figure 3A:
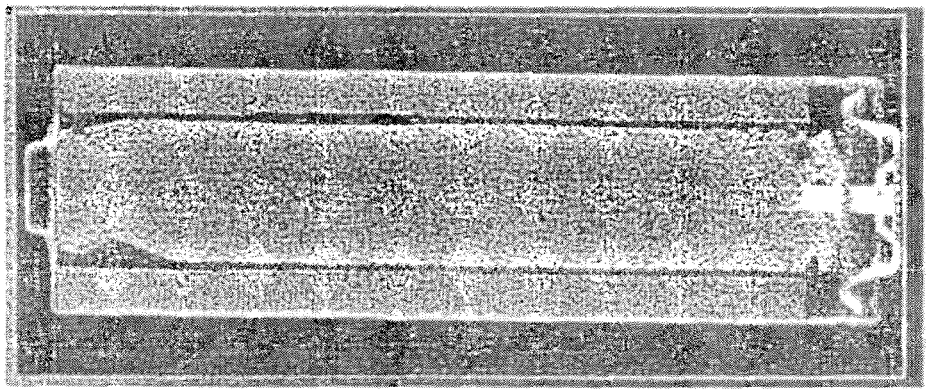
FIGS. 3A-3C are two-dimensional slices of three three-dimensional micro-computed tomography images of a AA battery.
Figure 3B:
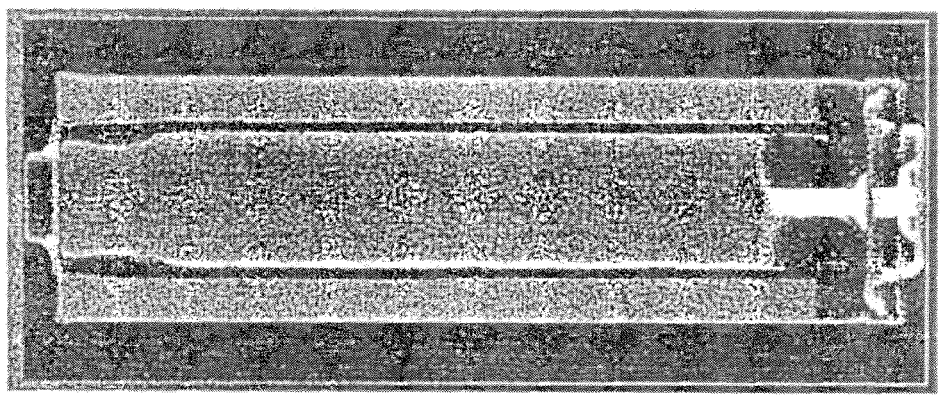

A commercial AA battery is provided and a three-dimensional structure is reconstructed from a mCT scan as shown in FIG. 3A. The AA battery is then vertically dropped along its length toward its pip (e.g., pip 26) for about 25 times. The three-dimensional structure from another mCT scan is plotted in FIG. 3B. Using the segmentation editor in Amira (Visage Imaging, Inc., CA), the volume of the non-woven component of the battery is calculated to be about 0.197 ml.

Figure 3C:
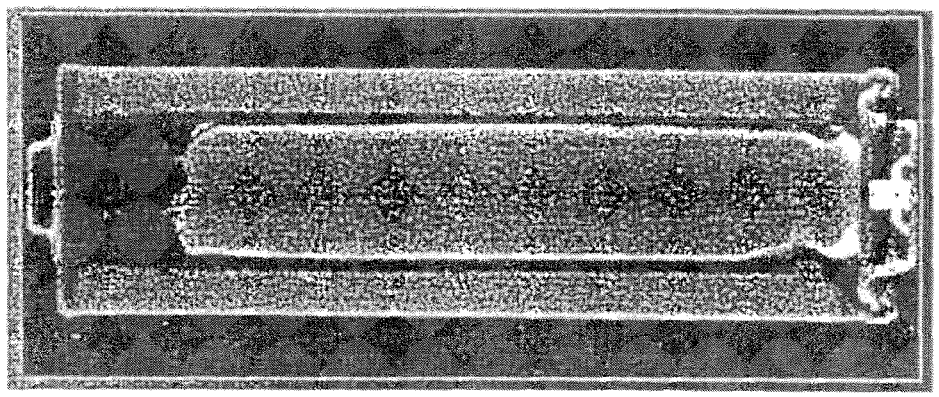

Next, the AA battery is drop vertically along its length toward the end cap (e.g., end cap 24) for about 50 times. The three-dimensional structure from another mCT scan is plotted in FIG. 3C. Using again the segmentation editor in Amira (Visage Imaging, Inc., CA), the volume of the non-woven component and the void of the battery is calculated to be about 0.560 ml. The void volume within the battery is then determined to be about 0.363 ml.

Other embodiments are within the following claims.

What is claimed is:

1. A method of determining a feature of a battery, the battery having an interior, the method comprising:
 (a) using micro-computed tomography to acquire data non-invasively for the interior of the battery; and
 (b) determining a volume or a density within the battery from the data.

2. The method of claim 1, wherein step (b) comprises determining a volume within the battery and the volume is occupied space.

3. The method of claim 1, wherein step (b) comprises determining the density at each of multiple positions in the interior of the battery.

4. The method of claim 1, wherein the battery comprises a cathode and step (b) comprises determining the density of the cathode.

5. The method of claim 1, wherein the density or the volume concerns a component of the battery.

6. The method of claim 1, wherein the battery comprises a cathode and step (b) comprises determining the cathode density at multiple positions in the interior of the battery.

7. The method of claim 4, wherein using the micro-computed tomography comprises applying X-ray beams from an X-ray source on the battery.

8. The method of claim 1, wherein the battery comprises a cathode and step (b) comprises determining the volume of the cathode.

* * * * *